(12) United States Patent
Hirschl (10) Patent No.: US 9,474,908 B2
(45) Date of Patent: Oct. 25, 2016

(54) BONE STABILIZER AND STIMULATOR IMPLANT

(71) Applicant: Robert Alex Hirschl, Clive, IA (US)

(72) Inventor: Robert Alex Hirschl, Clive, IA (US)

(*) Notice: Subject to any disclaimer, the term of this patent is extended or adjusted under 35 U.S.C. 154(b) by 0 days.

(21) Appl. No.: 14/312,955

(22) Filed: Jun. 24, 2014

(65) Prior Publication Data

US 2015/0251014 A1 Sep. 10, 2015

Related U.S. Application Data

(60) Provisional application No. 61/949,110, filed on Mar. 6, 2014.

(51) Int. Cl.
| | |
|---|---|
| *A61N 2/00* | (2006.01) |
| *A61N 2/06* | (2006.01) |
| *A61N 2/02* | (2006.01) |
| *A61B 17/70* | (2006.01) |
| *A61F 2/44* | (2006.01) |
| *A61B 17/80* | (2006.01) |
| *A61B 17/00* | (2006.01) |
| *A61F 2/28* | (2006.01) |

(52) U.S. Cl.
CPC .............. *A61N 2/002* (2013.01); *A61B 17/701* (2013.01); *A61B 17/7004* (2013.01); *A61B 17/7049* (2013.01); *A61B 17/7059* (2013.01); *A61B 17/7068* (2013.01); *A61B 17/80* (2013.01); *A61B 17/8095* (2013.01); *A61F 2/4455* (2013.01); *A61B 2017/00734* (2013.01); *A61F 2002/2821* (2013.01); *A61N 2/004* (2013.01); *A61N 2/02* (2013.01); *A61N 2/06* (2013.01)

(58) Field of Classification Search
CPC ............. A61N 1/362; A61N 1/36035; A61N 1/37217; A61N 1/36; A61N 1/37288; A61N 1/3756; A61N 1/3787; A61N 1/05; A61N 1/205; A61N 1/326; A61N 1/3605; A61B 17/72; A61B 17/8047; A61B 17/864; A61B 17/86; A61B 17/70; A61B 17/8061; A61C 8/0007
USPC ............. 606/305, 312, 331, 907, 60, 62–68; 607/51, 116, 149; 623/17.11–17.16, 623/16.11, 23.11, 20.32, 20.35, 24; 600/12
See application file for complete search history.

(56) References Cited

U.S. PATENT DOCUMENTS

| | | | |
|---|---|---|---|
| 3,842,841 A * | 10/1974 | Brighton et al. | ............... 607/52 |
| 4,414,979 A | 11/1983 | Hirshorn et al. | |
| 4,549,547 A | 10/1985 | Brighton et al. | |
| 5,292,252 A * | 3/1994 | Nickerson et al. | ........... 433/173 |
| 5,330,477 A | 7/1994 | Crook | |
| 5,413,596 A | 5/1995 | Kronberg | |
| 5,441,527 A | 8/1995 | Erickson et al. | |
| 6,034,295 A * | 3/2000 | Rehberg et al. | ........... 623/23.49 |
| 6,336,929 B1 * | 1/2002 | Justin | ................. A61B 17/7216 606/63 |
| 6,778,861 B1 | 8/2004 | Liebrecht et al. | |

(Continued)

FOREIGN PATENT DOCUMENTS

WO 0044435 A2 8/2000

*Primary Examiner* — Pedro Philogene
(74) *Attorney, Agent, or Firm* — John M. Behles (57) ABSTRACT

A dual function bone implant provides both stabilization and stimulation for bone healing. The implant includes a fixation or stabilization hardware body, with an electromagnetic field generator mounted in or on the body. The hardware body stabilizes the bone, while the electromagnetic field generator stimulates bone growth and fusion by producing an electromagnetic field at the bone site.

12 Claims, 7 Drawing Sheets

(56) References Cited

U.S. PATENT DOCUMENTS

| | | |
|---|---|---|
| 7,890,179 B2 * | 2/2011 | Wiegmann et al. ............ 607/51 |
| 7,917,223 B2 * | 3/2011 | Madjar et al. ................. 607/51 |
| 8,494,644 B2 | 7/2013 | Cowan et al. |
| 8,630,714 B1 | 1/2014 | Webb |
| 2012/0316482 A1 | 12/2012 | Karim |
| 2015/0080636 A1 * | 3/2015 | Rogachefsky ......... A61N 2/008 600/13 |

* cited by examiner

BONE STABILIZER AND STIMULATOR IMPLANT

CROSS-REFERENCE TO RELATED APPLICATIONS

This application claims priority under 35 U.S.C. §119 to provisional application Ser. No. 61/949,110 filed Mar. 6, 2014, herein incorporated by reference in its entirety.

BACKGROUND

Implants are well-known for use in stabilizing bone structures. Such implants take many forms, such as a cage, a plate, a rod, a crosslink, and/or spinous process clamp. It is also known that bone growth can be stimulated by exposure to electromagnetic fields which can be generated by an implanted device or an externally worn device. Both types of stimulators have problems. An implanted stimulator introduces an additional foreign object into the patient. Implanted stimulators also increase surgery time and potential complications. External bone stimulators require patient compliance, and have electromagnetic fields which are farther away from the healing site, compared to an implanted stimulator, thus weakening the field at the bone healing site.

Therefore, there is a need for improved bone stimulation and stabilization which overcomes the problems stated above.

Accordingly, a primary objective of the present disclosure is the provision of a combination bone stabilizer and stimulator implant.

A further objective of the present disclosure is the provision of a dual function bone implant having stabilization and growth enhancing electromagnetic fields.

A further objective of the present disclosure is the provision of a single implant device and for bone stabilization which produces an electromagnetic field adjacent the bone for hastened healing.

A further objective of the present disclosure is a provision of a bone implant for stabilization and stimulation which minimizes foreign matter in the body, decreases operative time and potential complications, and eliminates patient compliance issues.

Still another objective of the present disclosure is the provision of an implant device which is economical to manufacture and safe and efficacious in use.

These and other objectives become apparent from the descriptions of the following embodiments.

SUMMARY OF THE PRESENT DISCLOSURE

The bone stabilizing and stimulating implant of the present disclosure includes a fixation body having an electromagnetic field generator mounted therein. The fixation body may take various forms, such as a plate, a rod, a crosslink, a cage, or spinous process clamp. The electromagnetic field generator may be an electric current source, such as a battery, or a magnet, preferably made from a rare earth metal, such as neodymium iron boron. The dual function device is implanted into the patient's body adjacent the bone so that the fixation hardware stabilizes the bone and the electromagnetic field generator is adjacent the bone healing site to maximize the electromagnetic field effect to enhance bone growth.

Some embodiments include an implantable fixation body adapted for bone stabilization of a bone, wherein the implantable fixation body comprises: (a) at least one cavity on a surface of the implantable fixation body, the at least one cavity being: (i) defined by a sidewall; and (ii) further comprising an opening; and (b) rare earth magnet in fixed position within the implantable fixation body, disposed within the at least one cavity in such a way that at least one polar end of the rare earth magnet is: (1) oriented in alignment with the opening; and (2) in face-to-face proximate or contacting relationship with the bone, (3) the rare earth magnet being adapted to produce a static magnetic field for bone growth stimulation.

Some embodiments include an implantable device for bone stabilization and stimulation, comprising: (a) a fixation hardware member implantable to an internal site adjacent to bone to provide bone stabilization, wherein the fixation hardware comprises: (i) a rectangular cage having a wedge shaped head portion and slot aperture; (ii) a first surface of the rectangular cage comprising ridge lines that define channels and a second surface of the rectangular cage comprising ridge lines that define channels; and (iii) a rare earth magnet for generating a static magnetic field adjacent to the bone, the rare earth magnet comprising two poles, wherein the rare earth magnet is disposed within the slot aperture such that two poles of the rare earth magnet output the static magnetic field outwardly from the first surface and the second surface, to stimulate bone growth.

An example method of stimulating bone growth comprises: (a) implanting fixation hardware adjacent bone for bone stabilization; and (b) disposing within a pass through aperture of the hardware, a rare earth magnet having two poles, wherein the rare earth magnet is disposed in the pass through such that the two poles are exposed through openings of the pass through aperture, whereby the static magnetic field intersects with the bone to enhance bone growth.

DETAILED DESCRIPTION OF THE PREFERRED EMBODIMENTS

According to some embodiments, the preset disclosure is directed to a bone stimulator and stabilization implant that comprises an implantable fixation body that is adapted for bone stabilization of a bone. In some embodiments, the implantable fixation body comprises at least one cavity on a surface of the implantable fixation body that is defined by a sidewall. The sidewall defines an opening of the cavity. In some embodiments the opening receives a rare earth magnet for securement. The orientation of the magnet is optimized for promoting bone growth when the device is installed proximate a bone.

According to some embodiments, the rare earth magnet is placed in fixed position within the implantable fixation body. More specifically, the rare earth magnet is disposed within the at least one cavity in such a way that at least one polar end of the rare earth magnet is oriented in alignment with the opening. In some embodiments the polar end of the rare earth magnet is also in face-to-face proximate or contacting relationship with a bone of a patient.

In one or more embodiments, the rare earth magnet produces a static magnetic field for bone growth stimulation. The implantable fixation body can comprise any of a cage, a plate, a rod, a cross link, and a spinous process clamp—just to name a few. As mentioned above, the rare earth magnet can be manufactured from a neodymium iron boron material.

An example implant of the present disclosure includes a hardware or fixation body of various embodiments, such as a plate 10, a crosslink 20, a rod 30, a crosslink and rod assembly 40, a cage 50, and a spinous process clamp 60. The general shape of the hardware body may vary from that shown in the drawings without departing from the scope of the present disclosure.

Some embodiments of the implant also includes an electromagnetic field generator mounted on the hardware body. This electromagnetic field generator can be an electrical current source, such as a battery 12 mounted in the hardware body with wire leads 14 extending through the body and beyond. Alternatively, the electromagnetic field generator can be a magnet 16 secured in the hardware body. Preferably, the magnet is a rare earth metal, such as neodymium iron boron.

The battery 12 and electrical wiring 14 are shown in the drawings to be embedded in the hardware body. Alternatively, the battery and wires can be fixed to the exterior of the body. Similarly, the magnet is shown in the drawings as being embedded in the hardware body, but could alternatively be fixed to the exterior of the body. Such external positioning or mounted of the electromagnetic field generator to the hardware body may simplify manufacturing and eliminate concerns of weakening the body by providing a solid body without hollow channels or pockets for the electromagnetic field generator.

Each embodiment of the disclosure has the dual function of bone stabilization and stimulation. The hardware body provides the stabilization function, while the electromagnetic field generator provides the stimulation function.

Figure 1:
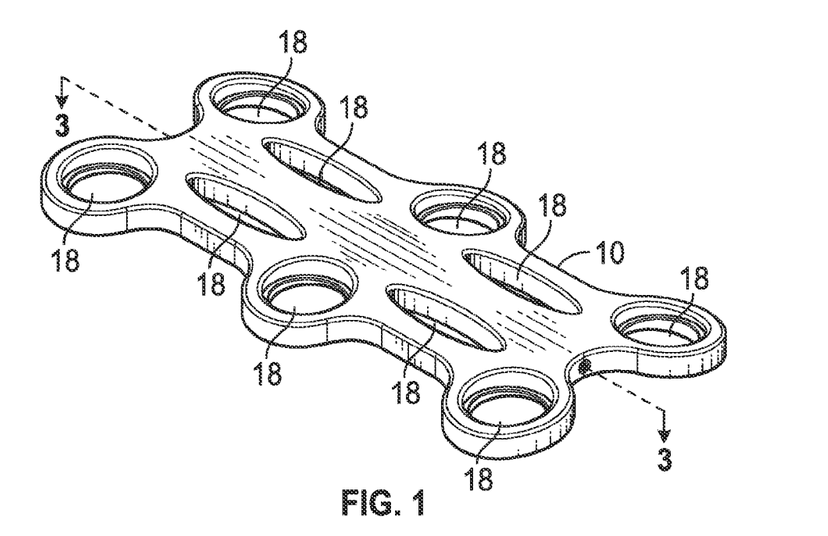
FIG. 1 is a perspective view of a first embodiment of the bone stabilization and stimulation implant according to the present disclosure.
Figure 2:
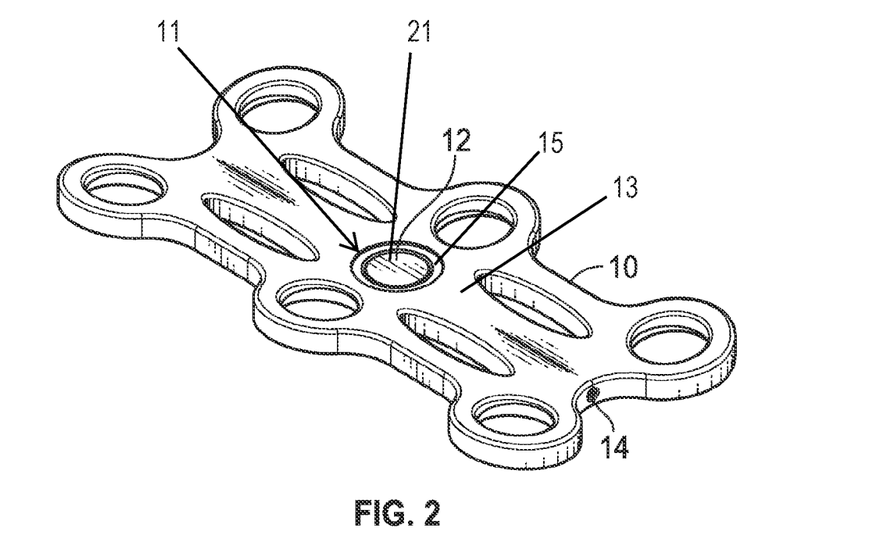
FIG. 2 is another perspective view of the first embodiment of the implant, shown from the opposite side as FIG. 1.
Figure 3:
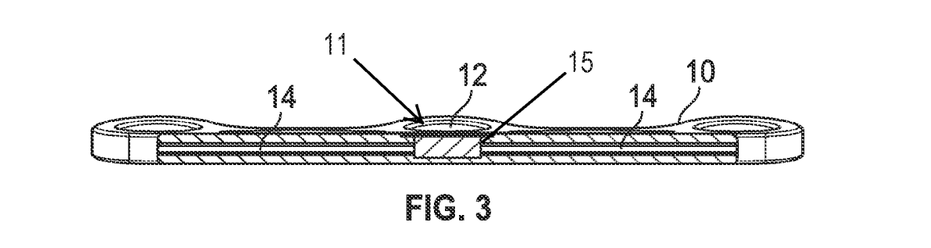
FIG. 3 is a sectional view of the first embodiment taken along line 3-3 of FIG. 1.

FIGS. 1-3 show a cervical plate 10 having a battery or rare earth magnet 12 mounted therein with wire leads 14 extending from the battery. The plate 10 includes convention holes 18 for receipt of conventional screws.

The cervical plate 10 comprises at least one cavity 11 on a surface 13 of the cervical plate 10. The at least one cavity 11 is defined by a sidewall 15. The sidewall 15 defines an opening of the cavity 11. In some embodiments the opening 11 receives a rare earth magnet 12 for securement. The orientation of the magnet 12 is optimized for promoting bone growth when the cervical plate 10 is installed proximate a bone.

According to some embodiments, the rare earth magnet 19 is placed in fixed position within the cervical plate 10 (e.g., in the cavity). More specifically, the rare earth magnet 12 is disposed within the at least one cavity in such a way that at least one polar end 21 of the rare earth magnet 12 is oriented in alignment with the opening. In some embodiments the polar end 21 of the rare earth magnet is also in face-to-face proximate or contacting relationship with a bone of a patient (not shown).

Figure 4:
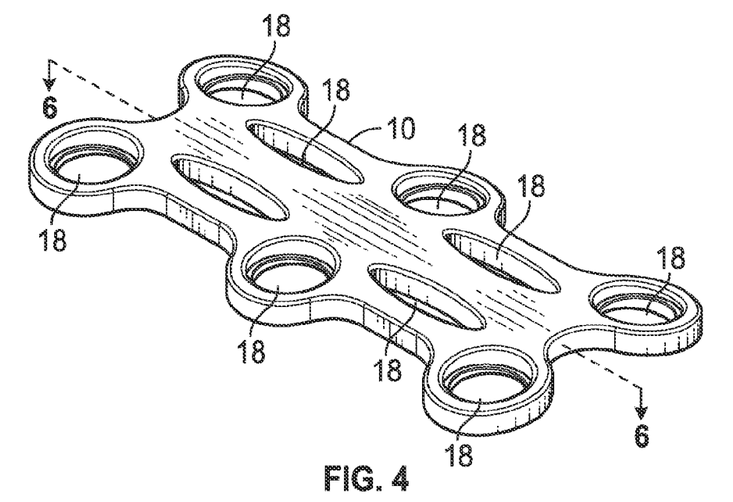
FIG. 4 is a perspective view of a second embodiment of the bone stabilization and stimulation implant according to the present disclosure.
Figure 5:
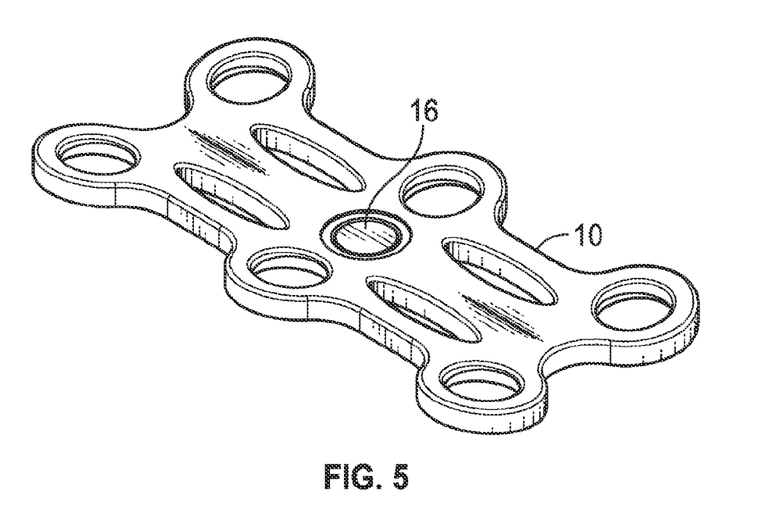
FIG. 5 is another perspective view of the second embodiment of the disclosure, taken from the opposite side as FIG. 4.
Figure 6:
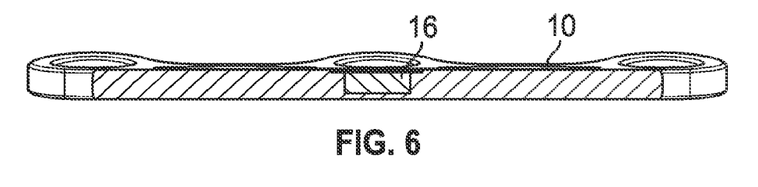
FIG. 6 is a sectional view of the second embodiment taken along line 6-6 of FIG. 4.

FIGS. 4-6 also show a cervical plate 10 with a magnet 16 mounted therein. The cervical plate implants of FIGS. 1-3 and FIGS. 4-6 function identically to one another.

Figure 7:
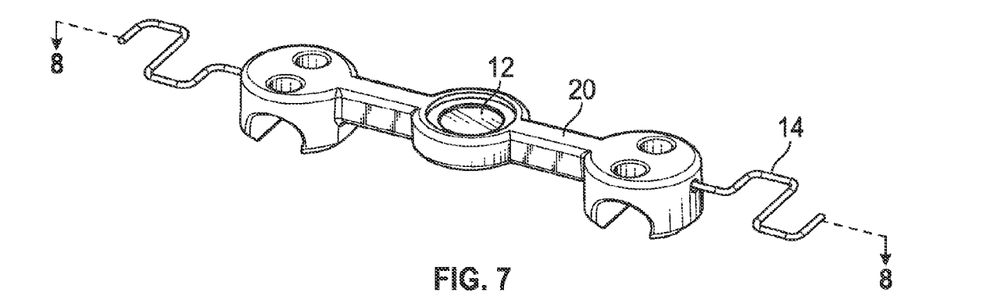
FIG. 7 is a perspective view of a third embodiment of the bone stabilization and stimulation implant of the present disclosure.
Figure 8:
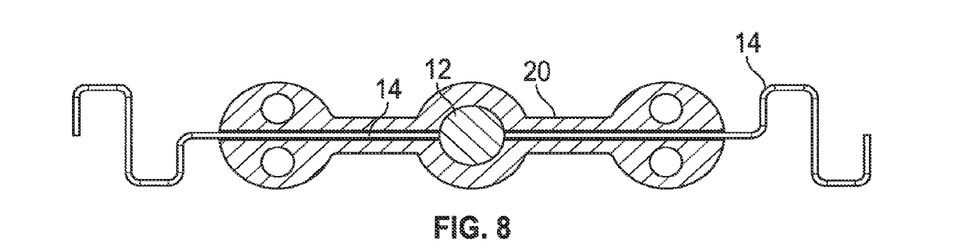
FIG. 8 is a sectional view of the third embodiment, taken along line 8-8 of FIG. 7.

FIGS. 7-8 show a crosslink hardware body 20 having a battery 12 mounted therein with wire leads 14 extending from the battery.

Figure 9:
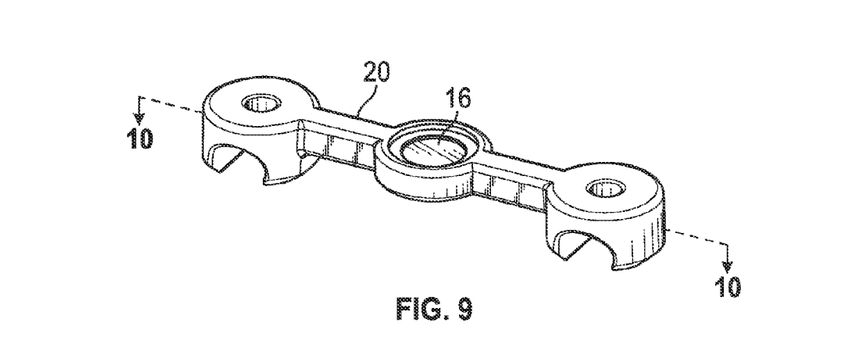
FIG. 9 is a perspective view of a fourth embodiment of the bone stabilization and stimulation implant according to the present disclosure.
Figure 10:
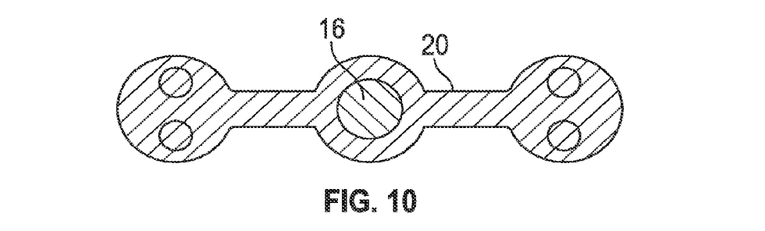
FIG. 10 is a sectional view of the fourth embodiment of the implant, taken along line 10-10 of FIG. 9.

FIGS. 9-10 show the crosslink 20 with a magnet 16 mounted therein, rather than the battery 12 and wires 14.

Figures 11, 12:
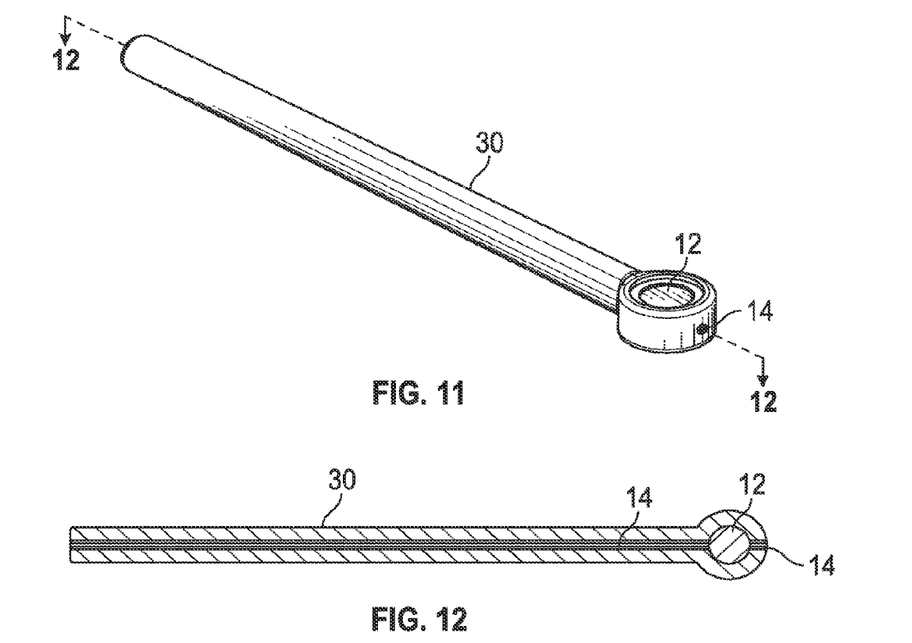
FIG. 11 is a perspective view of a fifth embodiment of the bone stabilization and stimulation implant, according to the present disclosure.
FIG. 12 is a sectional view of the fifth embodiment taken along lines 12-12 of FIG. 11.

FIGS. 11-12 show a rod 30 with a battery 12 mounted therein and wire leads 14 extending from the battery 12.

Figure 13:
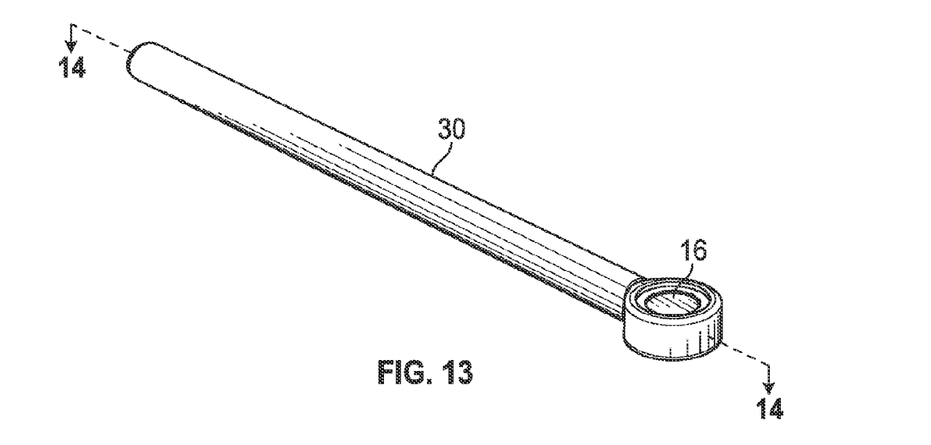
FIG. 13 shows a sixth embodiment of the bone stabilization and stimulation implant, according to the present disclosure.
Figure 14:
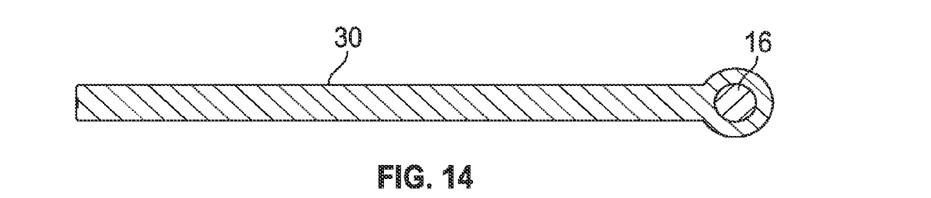
FIG. 14 is a sectional view taken along lines 14-14 of FIG. 13.

FIGS. 13-14 show the hardware rod 30 with a magnet 16 mounted therein.

Figure 15:
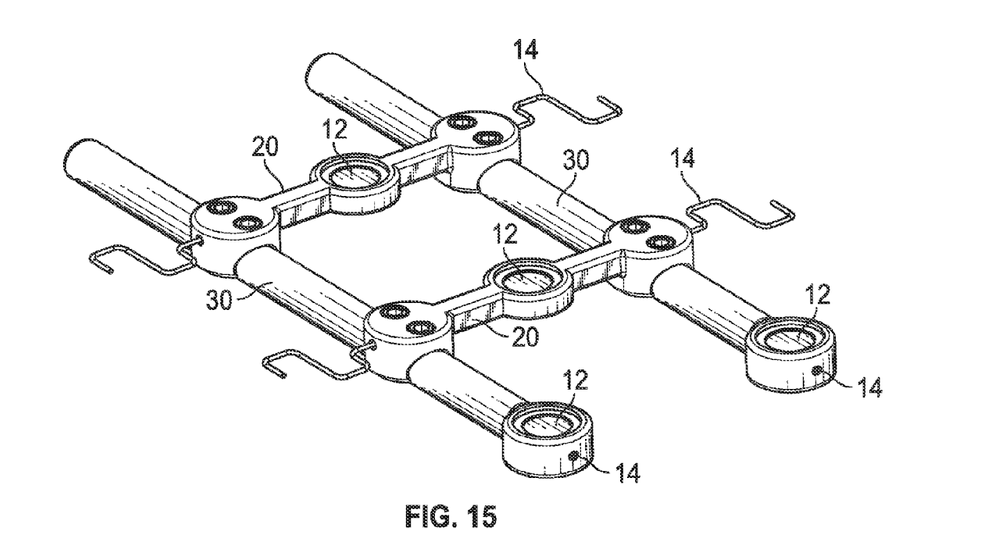
FIG. 15 shows an assembly utilizing the third and fifth embodiments of the implant from FIGS. 7 and 11.

FIG. 15 shows a plurality of crosslinks 20 and rods 30 assembled together to form a frame with the batteries 12 and wires 14. It is understood that this assembly can also use magnets, rather than the batteries and wires. Also, the assembly can be extended with additional crosslinks and rods, if needed.

Figure 16:
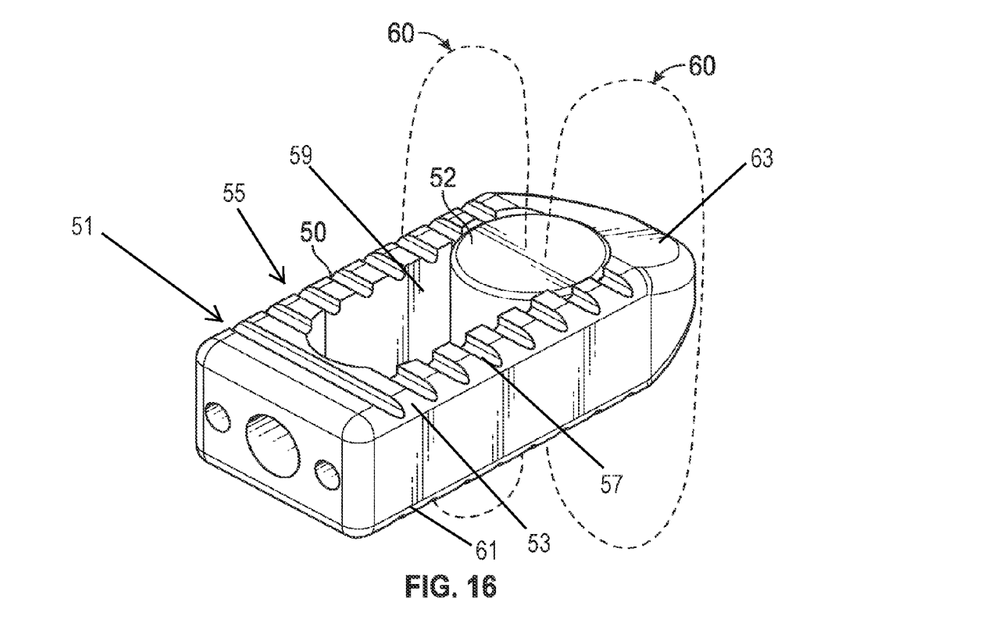
FIG. 16 is a perspective view of a seventh embodiment of a bone stabilization and stimulation implant, according to the present disclosure.
Figure 17:
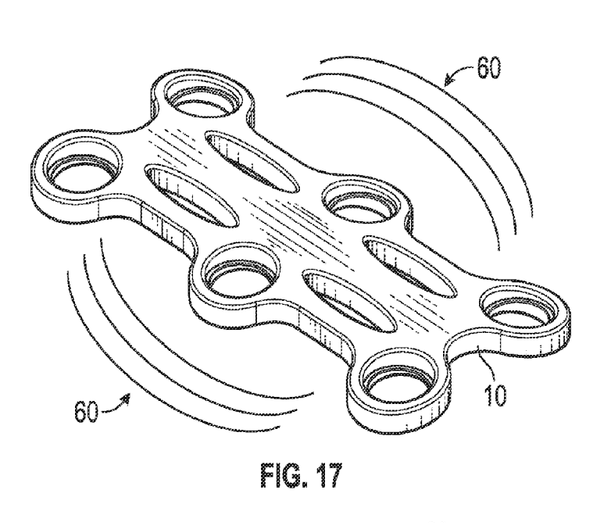
FIG. 17 is a perspective view of the second embodiment of the implant and its electromagnetic field.
Figure 18:
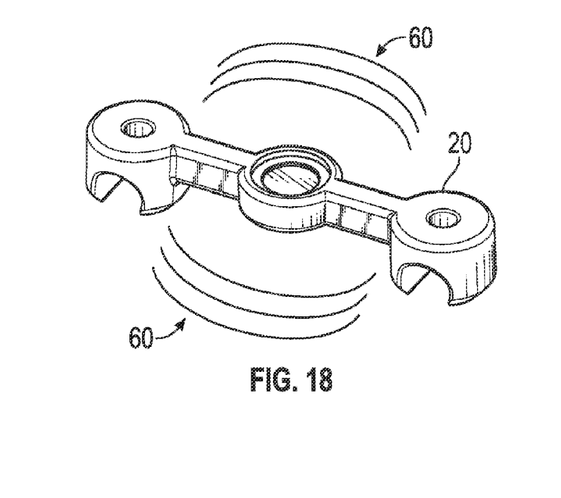
FIG. 18 is a perspective view of the fourth embodiment and its electromagnetic field.
Figure 19:
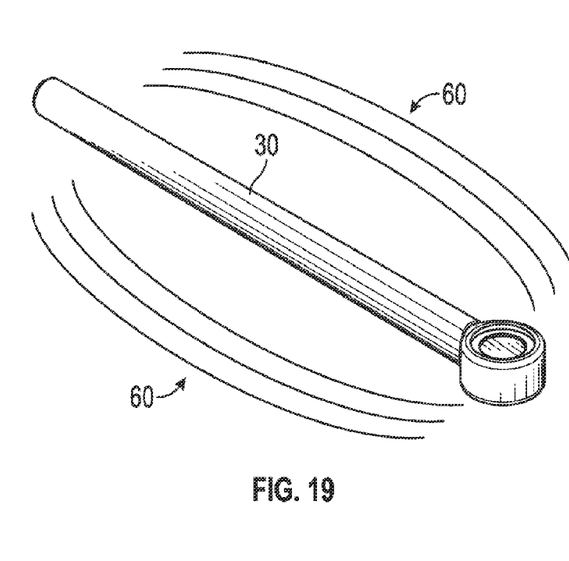
FIG. 19 is a perspective view of the sixth embodiment of the implant, with its electromagnetic field.

FIG. 16 shows a corpectomy cage 50 having a magnet 52 mounted therein. The magnet 52 has the same bone stimulation function as the magnet 16, but may have a different shape. The magnet 52 creates an electromagnetic field, represented by the broken lines in FIG. 16 and the reference numeral 60.

In more detail, the implantable device (corpectomy cage 50) is adapted for bone stabilization and stimulation. The corpectomy cage 50 comprises a fixation hardware member implantable to an internal site adjacent to bone to provide bone stabilization. The corpectomy cage 50 comprises a rectangular cage 51 having a wedge shaped head portion 63 and slot aperture 59 that receives the magnet 52. A first surface 53 of the rectangular cage 51 comprising ridge lines 55 that define channels 57 and a second surface 61 of the rectangular cage comprising ridge lines that define channels (these are not illustrated but are similar to the first surface 53).

In some embodiments, the magnet 52 is a rare earth magnet that generates a static magnetic field adjacent to a bone. In one embodiment, the rare earth magnet comprises two poles. The rare earth magnet is disposed within the slot aperture 59 such that two poles of the rare earth magnet output the static magnetic field outwardly from the first surface 53 and the second surface 61, to stimulate bone growth.

In a method of use of the corpectomy cage 50, an individual disposes within a pass through aperture (such as the of the slot aperture 59 of the corpectomy cage 50) of the hardware, a rare earth magnet having two poles. In some embodiments, the rare earth magnet is disposed in the pass through aperture such that the two poles are exposed through openings of the pass through aperture to allow the static magnetic field of the rare earth magnet to intersect with the bone to enhance bone growth.

FIGS. 16-19 show electromagnetic fields 60 generated by the battery 12 or the magnet 16 in the cervical plate 10, crosslink 20, rod 30, and cage 50, respectively.

Figure 20:
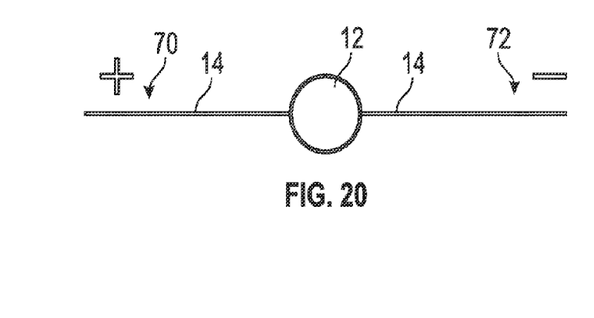
FIG. 20 is a schematic view showing the anode and cathode of an electric current source used in the first, third, and fifth implant embodiments.

FIG. 20 shows a schematic of the electric current source, including the battery 12 and the wires 14, with the opposite anode 70 and cathode 72 ends.

Figure 21:
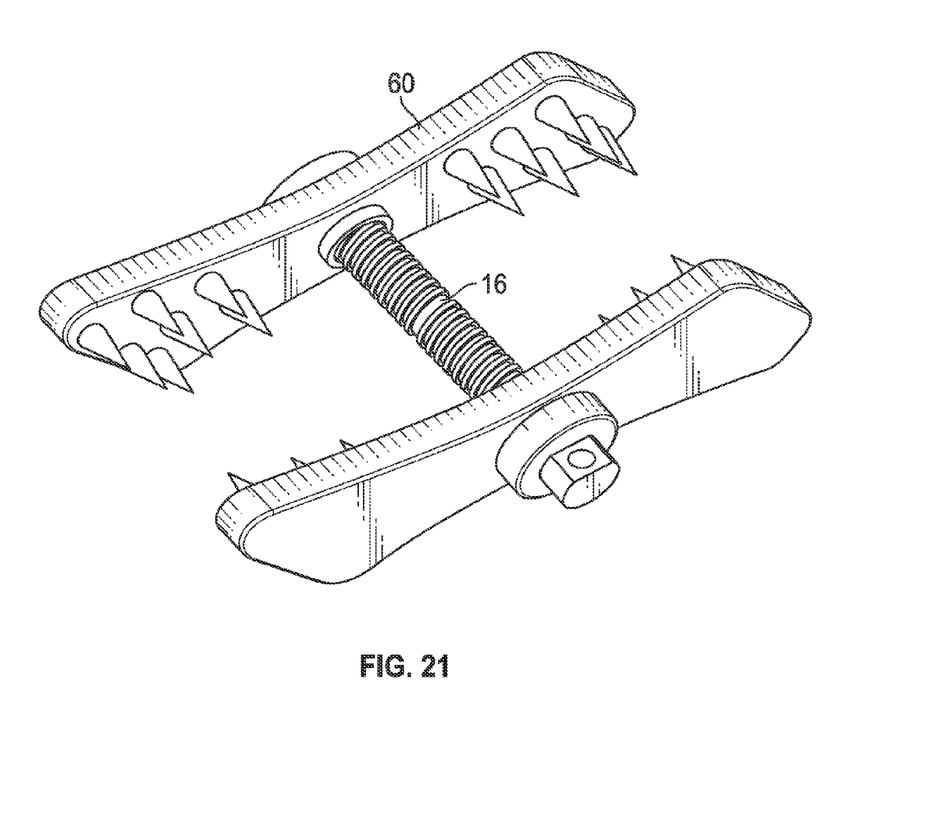
FIG. 21 is a perspective view of a seventh embodiment of the bone stabilization and stimulation implant, according to the present disclosure.

FIG. 21 shows the magnet 16 used in a spinous process clamp 60. It is understood that a battery 12 can also be used with the clamp 60, similar to the use of the battery 12 on the other hardware devices 10, 20, 30, 40 and 50. The magnet 16 is shown to be co-axial with the clamp axle, but the magnet 16 can be set in any position in the clamp 60.

The various embodiments of the implant of the present disclosure increases the chances of bone healing after surgery or trauma. The implants help promote bone healing by adding structural support from the hardware or fixation body, and bone growth and fusion stimulation from the electromagnetic field generator. This single apparatus provides multiple functions, as compared to the separate apparatus for each function. The single implant minimizes the amount or volume of foreign objects implanted into the patient, while decreasing operation times and complications. The implant of the present disclosure also eliminates any need for patient compliance, as with external bone stimulators. The implants also position the electromagnetic field as close as possible to the bone healing site, which is not possible with the stimulators which are separate from the stabilization hardware. The dual function implant also minimizes the surgical invasiveness, which was more extensive with the separate, single function implants which increased operation time, increased potential for infection and/or patient discomfort, and had the potential for movement from the desired position.

The process for implanting the dual function implants of the present disclosure would be known to one of ordinary skill in the art with conventional bone stabilization or fixation hardware. The disclosure has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A bone stimulator and stabilization implant, comprising:
    an implantable fixation body adapted for bone stabilization of a bone, wherein the implantable fixation body comprises:
        at least one cavity on a surface of the implantable fixation body, the at least one cavity being:
            defined by a sidewall; and
            further comprising an opening; and
    a rare earth magnet in fixed position within the implantable fixation body, disposed within the at least one cavity in such a way that at least one polar end of the rare earth magnet is:
        oriented in alignment with the opening; and
        in face-to-face proximate or contacting relationship with the bone,
    the rare earth magnet being adapted to produce a static magnetic field for bone growth stimulation.

2. The implant of claim 1 wherein the implantable fixation body is a cage.

3. The implant of claim 1 wherein the implantable fixation body is a plate.

4. The implant of claim 1 wherein the implantable fixation body is a rod.

5. The implant of claim 1 wherein the implantable fixation body is a cross link.

6. The implant of claim 1 wherein the implantable fixation body is a spinous process clamp.

7. The implant of claim 1 wherein the rare earth magnet is neodymium iron boron.

8. An implantable device for bone stabilization and stimulation, comprising:
    a fixation hardware member implantable to an internal site adjacent to bone to provide bone stabilization, wherein the fixation hardware comprises:
    a rectangular cage having a wedge shaped head portion and slot aperture;
    a first surface of the rectangular cage comprising ridge lines that define channels and a second surface of the rectangular cage comprising ridge lines that define channels; and
    a rare earth magnet for generating a static magnetic field adjacent to the bone, the rare earth magnet comprising two poles, wherein the rare earth magnet is disposed within the slot aperture such that two poles of the rare earth magnet output the static magnetic field outwardly from the first surface and the second surface, to stimulate bone growth.

9. The implantable device of claim 8 wherein the implantable fixation body is a cage.

10. The implantable device of claim 8 wherein the implantable fixation body is selected from a group comprising a plate, a rod, a cross link, a cage, and a spinous process clamp.

11. The implantable device of claim 8 wherein the rare earth magnet is neodymium iron boron.

12. A method of stimulating bone growth, comprising:
    implanting fixation hardware adjacent bone for bone stabilization; and
    disposing within a pass through aperture of the hardware, a rare earth magnet having two poles, wherein the rare earth magnet is disposed in the pass through such that the two poles are exposed through openings of the pass through aperture, whereby the static magnetic field intersects with the bone to enhance bone growth.

* * * * *